(12) United States Patent
Champ et al.

(10) Patent No.: US 6,676,951 B1
(45) Date of Patent: Jan. 13, 2004

(54) HOST-GUEST PROCESSES AND FORMULATIONS FOR DELIVERING BIO-AFFECTING COMPOUNDS

(76) Inventors: Charles Walton Champ, 17039 Turkey Point, San Antonio, TX (US) 78232; Karen June Kinzer, 17039 Turkey Point, San Antonio, TX (US) 78232

( * ) Notice: Subject to any disclaimer, the term of this patent is extended or adjusted under 35 U.S.C. 154(b) by 0 days.

(21) Appl. No.: 10/019,859
(22) PCT Filed: May 10, 2000
(86) PCT No.: PCT/US00/12743
§ 371 (c)(1), (2), (4) Date: Nov. 9, 2001
(87) PCT Pub. No.: WO00/67726
PCT Pub. Date: Nov. 16, 2000

Related U.S. Application Data

(60) Provisional application No. 60/133,552, filed on May 11, 1999.

(51) Int. Cl.[7] .................... A61K 9/00; A61N 25/34; B32B 15/02
(52) U.S. Cl. ............. 424/400; 424/404; 428/402
(58) Field of Search ................ 424/400, 401, 424/404, 484, 59, 78.01; 428/402.2, 402

(56) References Cited

U.S. PATENT DOCUMENTS

| | | | | |
|---|---|---|---|---|
| 5,326,567 A | * | 7/1994 | Capelli | 424/405 |
| 5,518,730 A | * | 5/1996 | Fuisz | 424/426 |
| 5,770,453 A | * | 6/1998 | Beer et al. | 436/149 |

* cited by examiner

*Primary Examiner*—Michael G. Hartley
(74) *Attorney, Agent, or Firm*—Crutsinger & Booth

(57) ABSTRACT

The invention relates to processes of making a composition having a host compound capable of accepting one or more bio-affecting guest compounds, and compositions formed by the processes. The processes comprise mixing, in any order: (i) a non-ionic surfactant selected from the group consisting of compounds having chemical structure (I) where "—CH—O—CH—" represents an epoxide group, where $R_a$ and $R_b$ are hydrocarbons that can be the same or different, where at least one of the $R_a$ and $R_b$ hydrocarbons includes an epoxide group within 3 carbons of the hydrocarbon attachment to contribute to the desired hydrolipid balance of 7–9, where $R_c$ is hydrogen or a methyl group, and where $R_d$ is a methylene group, and ethyl group, or a structurally equivalent link with a bond length range about the same as or shorter than that provided by an ethyl group, and having a hydro-lipid balance in the range 7–9; (ii) an amphoteric surfactant selected from the group consisting of organic compounds having the chemical formula $NH_3$—R—COOH, where R is a straight, branched, or aromatic hydrocarbon structure having 6–24 carbons; (iii) a solvent for the amphoteric surfactant; (iv) an aromatic selected from the group consisting of compounds having at (I) least one aromatic five or six-member ring; (v) an aluminum cation; (vi) a Lewis acid that is not a Bronsted-Lowry acid; and (vii) a Bronsted-Lowry acid.

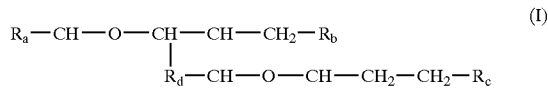

30 Claims, 4 Drawing Sheets

18 Crown 6 Formation

EO-3 nonionic branched chain surfactant

NOTE: $Al_2(SO_4)_3 + H_2O \rightleftharpoons Al_2(SO_4)_3 + H_2O + H_2SO_4 + Al(OH)_3$ pH=3.1
Balanced with zwitterion

ALTERNATIVE 1

ALTERNATIVE 2

CALIXERAND

CALIXERAND

HOST-GUEST PROCESSES AND FORMULATIONS FOR DELIVERING BIO-AFFECTING COMPOUNDS

This is an application under 35 U.S.C. §371 of PCT/US00/12743, filed May 10, 2000, which claims the benefit of U.S. provisional application Ser. No. 60/133.552, filed May 11. 1999.

FIELD OF THE INVENTION

The present invention relates to processes and formulations capable of protecting, stabilizing, and/or delivering one or more bio-affecting compounds. More particularly, the invention relates to processes of making a composition having a host compound capable of accepting one or more bio-affecting guest compounds and new compositions formed by the processes. The processes are particularly useful in formulating compositions for the topical delivery of the bio-affecting compounds.

BACKGROUND OF THE INVENTION

Biological systems depend on a balance between water-soluble compounds and fat-soluble compounds. Frequently, natural enzymatic reaction will convert a compound to help maintain the balance between water-soluble compounds and lipid-soluble compounds in the biological system, for example, ascorbyl palmitate, which is lipid soluble, can be converted by enzymatic action to ascorbic acid, which is water soluble.

The flow of both water-soluble and lipid-soluble compounds into and out of biological systems are controlled by cell membranes. To penetrate a membrane, a compound needs to have an appropriate structure. In addition, the transfer of the compound across a cell membrane is governed by enzymes, pH, and salt balance. Thus, the cell membranes also help maintain the balance between water-soluble compounds and lipid-soluble compounds in the biological system.

The formation of compositions capable of delivering a compound to a cell membrane and in a structural form or environment that will encourage the transfer of the compound across the cell membrane into the biological system has been the subject of considerable research using many different approaches.

For example, it is known that ascorbic acid (Vitamin C) can be beneficial for healing the skin. In a composition for topical application to the skin, a relatively high concentration of ascorbic acid, preferably at least 8% by weight of the composition, is desirable, and perhaps necessary, to be effective in penetrating the dermal layer and activating collagen in the skin. When the ascorbic acid composition is exposed to air, however, and particularly at such high concentrations, the ascorbic acid tends to rapidly oxidize. A stabilizing environment for the ascorbic acid is necessary to protect it from oxidation or the composition will lose its effectiveness.

It is also known that alpha tocopherol (Vitamin E) can be beneficial for healing and/or preventing damage to the skin by scavenging free radicals in the biological system. In a composition for topical application to the skin, a relatively high concentration of alpha tocopherol, preferably at least 5% by weight of the composition, is desirable, and perhaps necessary, to be effective in penetrating the dermal layer and reducing free radicals. When the alpha tocopherol composition is exposed to air, however, the alpha tocopherol tends to oxidize, that is, become rancid. A stabilizing environment for the alpha tocopherol is necessary to protect it from becoming rancid or the composition will lose its effectiveness.

Considerable research has been conducted on stabilizing ascorbic acid, which is water soluble, and on stabilizing alpha tocopherol, which is lipid soluble. Because of their widely-different solubility characteristics, however, obtaining high concentrations of both in the same composition continues to be a particular challenge. Many compositions for topical application contain low concentrations of both ascorbic acid (as a preservative) and alpha tocopherol (as an antioxidant) at levels below 0.5% by weight. At these low concentrations, however, the ascorbic acid and alpha tocopherol are much less effective in repairing skin damage.

Furthermore, compositions having high concentrations of certain bio-affecting compounds, such as ascorbic acid, have been particularly difficult to stabilize. In this regard, standard stability test procedures that are used to determine the shelf life of a product do not tell the whole story. A standard stability test is conducted at elevated temperatures and humidity is commonly used for determining the shelf life of a composition. Because the rates of chemical reactions and the growth of bacteria tend to double with each 10° C. (18° F.) increase in temperature, testing the stability of a product at elevated temperatures can be used to calculate its expected shelf life at ordinary temperatures with a reasonable degree of confidence. The standard test requires the compound to be placed in the sealed container in which it is to be sold or stored, for 30, 60, and 90 days at 31° C. (87° F.) and at 45° C. (113° F.) in a chamber at 80% relative humidity. This test does not, however, determine the stability of the product after the sealed container has been opened. Unfortunately, many products that pass the shelf-life stability test become unstable in a much shorter period of time once the container has been opened, and quickly lose effectiveness, and worse, may allow the growth of pathogenic bacteria.

Another type of problem encountered in designing topical delivery systems for bio-affecting compounds is encountered when the bio-affecting compound is virtually or totally insoluble in either water or lipids. For example, bio-affecting ingredients for ultra-violet sun block protection include zinc oxide (ZnO) and/or titanium dioxide ($TiO_2$), lo which can be used for blocking UV-A and/or UV-B radiation, respectively. Unfortunately, it is difficult to find a carrier for evenly dispersing these insoluble inorganic compounds in a sufficient concentration to form a protective layer over the skin without also imparting a whitening color, which most people find aesthetically undesirable.

There has been a long-felt need for a process of formulating a composition that would be capable of stabilizing at least two different bio-affecting compounds having diverse solubility characteristics. Such a process can be used to stabilize only one bio-affecting compound, but it is expected to have particularly beneficial use when it is desirable to prepare a composition having at least two different bio-affecting compounds of diverse solubility characteristics. There has also been a long-felt need for a process of formulating a composition that is capable of protecting and stabilizing high concentrations of certain bio-affecting compounds that have been particularly difficult to stabilize at such high concentrations. In addition, there has been a particular long-felt need for a process of formulating a composition that is capable of remaining stable for long periods of time, even after the container has been opened causing the composition to be exposed to the ambient air environment. It would also be desirable to produce a composition that discourages the growth of bacteria. These problems have been particularly acute with respect to compositions and products that are expected to be used over an extended period of time after the sealed container has been opened. By way of further example, there has been a long-felt need for a topical delivery system capable of evenly dispersing a bio-affecting compound that is insoluble.

SUMMARY OF THE INVENTION

The formulation processes and compositions according to the invention depend on the initial formation of a host composition having a host capable of accepting a guest in host-guest coordination. One or more bio-active compounds can then be mixed with the host composition for creation of a stable molecular environment, that is, according to a process of molecular stacking. For compositions including water, the formulation processes preferably include establishing a desired pH range to help maintain the stability of pH-sensitive compounds. A wide range of bio-affecting compositions can be made according to the general approach of the invention. In addition, specific formulation processes and compositions are provided.

According to a general aspect of the invention, a process is provided for making a host composition having a host for at least one guest, the process comprising mixing, in any order:

(i) a non-ionic surfactant selected from the group consisting of compounds having a chemical structure:

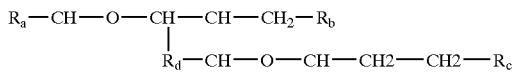

where "—CH—O—CH—" represents an epoxide group,
where $R_a$ and $R_b$ are hydrocarbons that can be the same or different,
where at least one of the $R_a$ and $R_b$ hydrocarbons includes an epoxide group within 3 carbons of the hydrocarbon attachment to contribute to the desired hydro-lipid balance of 7–9,
where $R_c$ is hydrogen or a methyl group, and
where $R_d$ is a methylene group (—CH$_2$—), an ethyl group (—CH$_2$—CH$_2$—), or
a structurally equivalent link with a bond length range about the same as or shorter than that provided by an ethyl group, and
having a hydro-lipid balance in the range of 7–9,
or any combination of two or more thereof;

(ii) in a stoichiometric proportion of at least 1:6 relative to the non-ionic surfactant, an amphoteric surfactant selected from the group consisting of organic compounds having the chemical formula NH3—R—COOH, where R is a straight, branched, or aromatic hydrocarbon structure having 6–24 carbons, or any combination of two or more thereof;

(iii) at least a sufficient amount of a solvent to dissolve the amphoteric surfactant, the solvent comprising one or more compounds selected from the group consisting of water, alcohols having straight or branched hydrocarbon structure having up to 6 carbons, glycosamionoglucans, or any combination of two or more of the foregoing:

(iv) in a stoichiometric proportion of at least 1:240 relative to the non-ionic surfactant, an aromatic selected from the group consisting of compounds having at least one aromatic five or six-member ring structure, or any combination of two or more thereof.

(v) in a stoichiometric proportion of at least 1:240 relative to the non-ionic surfactant, of an aluminum cation;

(vi) in a stoichiometric proportion of at least 1:1200 relative to the non-ionic surfactant of at least one Lewis acid that is not a Bronsted-Lowry acid;

(vii) at least 0.003 molar concentration of at least one Bronsted-Lowry acid.

Without being limited by suggesting a theoretical explanation at the molecular level for how these ingredients react to create a host composition, it is believed that a process according to this general approach is capable of producing a composition having one or more host molecular complexes such as crown ethers, crystahemispherands, calixerands, calixarenes, carcerands, rotoxanes or other host molecular configurations capable of forming a host-guest relationship with guest molecular structures, which is accomplished without the use of a guest transitional metal. Instead of a transition metal, it is believed that a five- or six-member aromatic ring structure is of the appropriate molecular size and provides the appropriate electron orbitals to coordinate in the formation of the host complex. After the initial formation of a host composition having a host complex, a bio-affecting compound, either organic or inorganic, can be mixed with the host composition according to the formulation processes for creation of a stable molecular environment, that is, according to a process of molecular stacking.

The particular compounds used can be varied according to the principles of the invention dependent on the desired molecular stacking parameters for stabilizing one or more bio-affecting ingredients. For example, nonoxyl-9, which includes a phosphate group that can be considered to be a Lewis acid but not a Bronsted-Lowry acid, can be used for providing both the aromatic and the Lewis acid. Nonoxyl-9 has the further advantage of being a well-known germicide. By way of another example, in a composition including water, aluminum sulfate, which in water forms a small amount of sulfuric acid, can be used for providing both the aluminum cation and the Bronsted-Lowry acid.

As will hereinafter be described in more detail, and illustrated by way of representative examples, the relative proportions of these compounds can vary considerably without departing from the scope of the invention.

According to a further aspect of the invention, one or more compounds are selected to be sequentially mixed with the host composition to form a stable molecular environment, which is sometimes referred to herein as a process of molecular stacking. The sequence of mixing the additional bio-affecting compounds is based on the following factors:

(i) the one or more desired bio-affecting compounds to be added to create a desired composition for a specific application; and (ii) the desired point of attachment to the host complexes.

The systematic addition, i.e., molecular stacking, of the bio-affecting and other desirable ingredients into the host composition is also based on a consideration of the following factors:

(i) the molecular structure of each ingredient;

(ii) the solubility of each ingredient compound and the hydro-lipid balance of the composition, and the possibility of changing the solubility characteristics by changing the form of the ingredient, e.g., by using a salt form of the ingredient;

(iii) in an aqueous composition, the effect of each ingredient on the pH, and the sensitivity of each ingredient to pH; and (iv) the temperature required for "setting" or "stacking" the ingredient into the host composition.

In formulation processes including water, the process preferably includes establishing a desired pH range to help maintain the stability of pH-sensitive compounds. Establishing the desired pH range often has a substantial influence on the selection of one or more additional compounds to be mixed with the host composition and the mixing sequence.

Those skilled in the art will appreciate that a wide range of bio-affecting compositions can be made according to the general approach of the invention. In addition, specific formulation processes and compositions are provided for various bio-affecting compositions, which compositions are highly effective for certain biological purposes, such as skin exfoliation, collagen activation in the skin, the topical delivery of salicylic acid, and other pain relievers to local areas of pain and/or inflammation, to promote skin healing processes, and other purposes, such as the delivery of plant growth hormones, such as diterpenes, or even the topical dispersion of UV radiation blocking compounds. Thus, the formulation processes according to the invention are expected to be useful in the production of a wide array of compositions having bio-affecting purposes.

As used herein, water soluble means that a compound or mixture of compounds has a solubility characteristic of at least 0.2 g/100 g of distilled water at standard temperature and pressure. To the extent the compound or mixture of compounds does not meet this solubility criteria, it would be expected to be lipid soluble. It is to be understood that this bright-line criteria between water solubility and lipid solubility is arbitrarily assigned as a matter of clarity of definition, and that the solubility characteristics in relation to complex mixtures can be blurred by factors such as temperature, pressure, pH, chemical reaction, complex coordination, and mutual solubility. Of course, some compounds, particularly inorganic compounds, can be nearly or completely insoluble in both water and lipids.

For example, a process according to the invention can be used to formulate specific compositions including one or more compounds that can be considered to be water soluble selected from the group consisting of: ascorbic acid, ascorbyl salts, 7-dehydroxy cholesterol, alpha-hydroxy acids, beta-hydroxy acids, glycolic acids, isoprenoids, bioflavinoids, fatty acids, glycosaminoglucans, flavin mono nucleotides, flavin mono nucleotide derivatives, diterpenes, glycerophospholipids, beta-carotene, trans retinol, trans retinoic acid, allontoin, nonoxyl-9, betaine, and any combination of two or more of the foregoing.

A process according to the invention can be used to formulate specific compositions including one or more compounds that can be considered to be lipid-soluble selected from the group consisting of: alpha tocopherol, alpha tocopherol ester, co-enzymes, ubiquinones, menaquinones, phylloquinones, 7-dehydroxycholesterol, steroids, bioflavinoids. terpenes, saponified fatty acids, unsaponified fats, alycerophospholipids, and any combination of two or more of the foregoing.

Similarly, the host complexes can be used for a variety of formulations that do not require direct activation of ingredients in response to the system in which they are introduced. Rather, the stabilization of crown complexes can provide an alternative at the other end of the spectrum of products. By way of further example, a process according to the invention can be used to formulate specific compositions including one or more compounds that can be considered to be nearly or completely insoluble in either water and lipids, such as inorganic compounds, and more particularly, titanium dioxide and/or zinc oxide. The processes according to the invention allow for the inclusion of non-hydrocarbon chemicals that are bio-affecting as not only resistant to external forces (like UV radiation) within mammalian systems, but also provide the consistent ability to release other organic products as a resultant of the interacting system.

It is important to note, however, that solubility characteristics of chemical compounds are typically reported based on studies of a purified form of the particular chemical. Many naturally-occurring chemicals are found and extracted in conjunction with derivatives that substantially affect solubility of the naturally-occurring mixtures.

General Objects of the Invention

The invention has one or more of the following illustrative objects, which are not intended to limit the invention to being able to accomplish all of the following objects:

(a) to provide a host composition having a host capable of accepting at least one bio-affecting guest for use in topical delivery of the bio-affecting guest to the mammalian skin/dermal layer or plant membrane of a target biological system;

(b) to provide a host composition capable of stabilizing a sufficiently high concentration of one or more bio-affecting compounds to activate the natural biochemical pathways after delivery to and penetration through the mammalian ski n/dermal layer or plant membrane of a target biological system;

(c) to create a molecular environment that is capable of protecting and stabilizing at least two bio-affecting compounds that have widely-different solubility characteristics:

(d) to create a molecular environment and coordinated complex that will release one or more bio-affecting compounds to the membrane of a target biological system; and/or (e) to provide specific formulations and compositions for the topical delivery of the bio-affecting compounds.

BRIEF DESCRIPTION OF THE DRAWING

The accompanying views of the drawing are incorporated into and form a part of the specification to illustrate several aspects and examples of the present invention. These figures together with the description serve to explain the principals of the invention. The figures are only for the purpose of illustrating preferred and alternative examples of the various aspects of the invention and are not to be construed as limiting the invention to only the illustrated and described examples. The various advantages and features of the various aspects of the present invention will be apparent from a consideration of the drawings in which.

DETAILED DESCRIPTION OF PRESENTLY PREFERRED EMBODIMENTS

Figure 1:
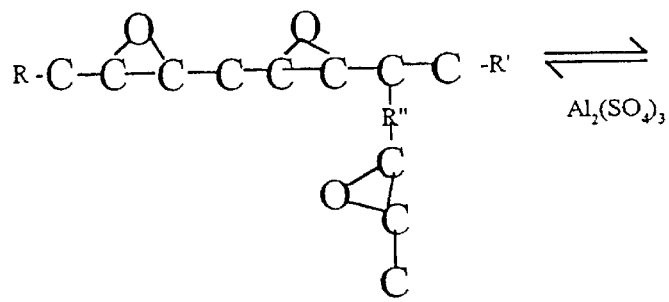
FIG. 1 illustrates the formation of an 18 crown 6.
Figure 1:
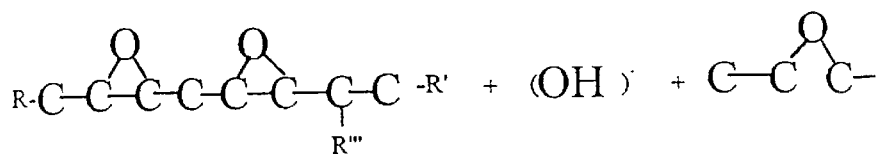
Figure 1:
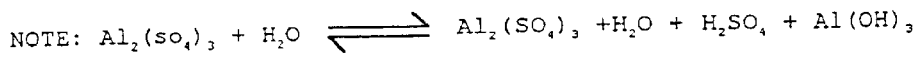
Figure 1:
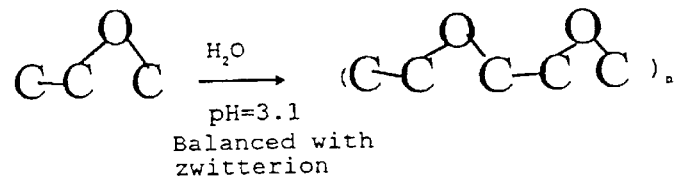
Figure 1:
Figure 1:
Figure 1:
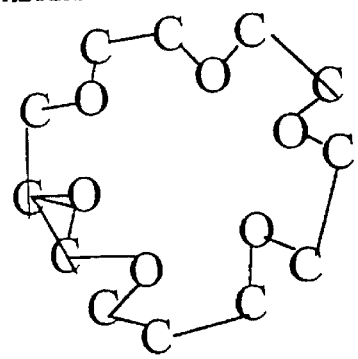
Figure 1:
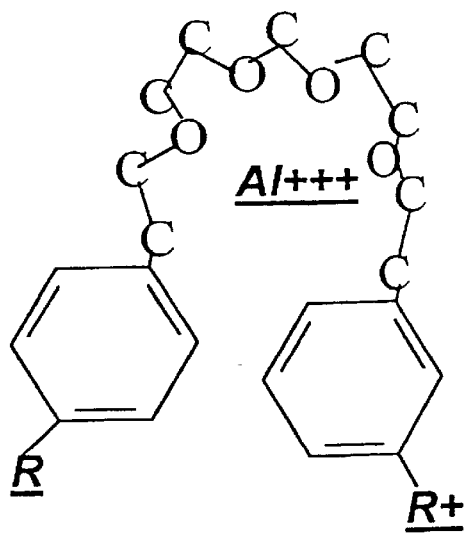

The formulation processes and compositions according to the invention depend on the initial formation of a host composition capable of accepting a guest in host-guest coordination. Thereafter, one or more bio-active compounds can be mixed with the host composition according to the formulation process for creation of a stable molecular environment for the bio-active compounds, that is, according to a process of molecular stacking.

A. Formulation of a Host Composition

1. Crown Ethers and Other Host Compounds

Crown ethers were first discovered by Charles Pederson in 1967. Crown ethers act as ionophores trapping guest atoms or molecules that would otherwise not be able to transfer across membranes because the trapped molecule is not soluble in the fatty compounds found in the membrane. Traditionally, the guest has been a transition metal. Crown ethers tend to mimic enzymes in function because they act as carriers of other compounds across membranes. The most commonly occurring crown ether structure in biological systems is ferrechrome which has hemoglobin at the center of a C—N—O ether ring. Other forms of host molecules include, for example, crystahemispherands, calixarenes, carcerands, and rotoxanes. It is important to recognize that all these host compounds are not necessarily cyclic in nature, but many are actually open crowns that are generally horse-shoe shaped.

With the presence of transitional metals, crown ethers are more rigid and interlocking similar to amino acid building blocks in DNA. Without the presence of a transitional metal, the crown ethers tend to be flat and soft, more like a rubber band, and without the presence of a well-defined cavity. To act as a host, a guest molecule must be present to give the crown ether or other host compound its shape and function.

Crown ethers are typically formed and stabilized with transitional metals and acyl or acetyl groups by establishing a catalytic reaction which allows for synthesis of a crown ether including repeating (—C—O—C—)$_n$ groups and stabilized by electrophilic attraction. The larger the transitional metal, the larger the crown ether formed with the transition metal.

After being formed, crown ethers and other forms of host complexes can attach to cyclic and aromatic compounds. These host forms allow for attachment or coordination of molecules having widely-different solubility characteristics. Of course, these host complexes can also allow for attachment or coordination with inorganic compounds, such as transition metal compounds, which may be virtually or completely insoluble in either water or lipids.

2. Surfactants

Surfactants in water can create lamellar configurations, vesicles, micelles, and reverse micelles which will incorporate compounds that have the opposite solubility of the chemical system, water in oil, oil in water. These configurations align the polar end of a molecule in one direction and the non-polar end in the opposite direction. The specific configuration will vary dependent upon the type of surfactant, the concentration of the surfactant, the compound (s) involved, temperature, and mix order of the compounds. Generally, surfactants will create an emulsion or a microemulsion. Surfactants also alter the interfacial tension of the chemical system. Low temperatures and/or elevated pressures will cause separation of the oil and water phases in a surfactant system.

Examples of surfactant systems are found naturally in biological systems, the most prominent is the lung surfactant containing 50% to 60% dipalmitoylphosphatidyl choline. The lung surfactant maintains high surface tension preventing collapse of the alveoli upon air expulsion from the lungs. The phophatidyl choline is a phopholipid which will also create electron orbitals that will share with both lipid and water-soluble compounds. In combination with certain bio-affecting compounds, the stability of that compound is lessened.

3. New Method of Making Host Compounds With Surfactants

According lo the presently preferred embodiment of the invention, a transitional crown ether "host" can be formed in a what is referred to herein as a "host composition." The tdiversely-soublensitional crown ether allows for electrophilic attachment of diversely-soluble compounds.

A host complex is created by using a combination of non-ionic and amphoteric surfactant in an aqueous environment with aluminum sulfate. The non-ionic surfactant is selected from the group consisting of compounds having the following chemical structure:

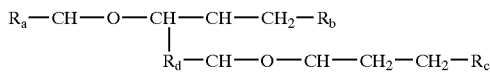

where "—CH—CH—" represents an epoxide group, where $R_a$ and $R_b$ are hydrocarbons that can be the same or different, where at least one of the $R_a$ and $R_b$ hydrocarbons includes an epoxide group within 3 carbons of the hydrocarbon attachment to contribute to the desired hydrolypid balance of 7–9, where $R_c$ is hydrogen or a methyl group, and where $R_d$ is a methylene group (—CH$_2$—), an ethyl group (—CH$_2$—CH$_2$—), or a structudiversely-solublelly equivalent link with a bond length diversely-solublenge about the same as or shorter than that provided by an ethyl group, and having a hydro-lipid balance in the diversely-solublenge of 7–9, or any combination of two or more thereof It is believed that the epoxide group included with $R_a$ or $R_b$ is necessary to contribute to the desired hydrolypid balance of 7–9 of the non-ionic surfactant. More prefediversely-solublebly, $R_a$ includes the required epoxide group. Most preferably. $R_c$ is a hydrogen. Without being limited by this theoretical explanation, it is believed, and as further supported by conformational analysis and preliminary GC mass spectral analysis data, that the —CH—O—CH—CH$_2$—CH$_2$—R$_c$ group of this type of structure is susceptible to being cleaved from $R_d$, which cleaved group further reacts to provide the chemical structural building blocks for the creation of a host complex, probably a crown ether, and probably an 18-crown-6 ether. To form a perfect crown ether structure, $R_c$ is most preferably hydrogen.

As used herein, "hydrocarbon" generally refers to a chemical structure made up of hydrogen and carbon atoms. Unless the context clearly requires otherwise, however, it is to be understood that the term does not exclude hydrocarbon structures having other atoms or chemical functionalities, so long as such variations do not interfere with the chemistry of the formulation processes and compositions.

The presently most preferred components for the formation of the host composition are:

(i) a branched chain non-ionic surfactant having the chemical structure R-(CH$_2$)$_1$-2,3-epoxide-(CH$_2$)$_4$-8,9-epoxide-CH$_2$)$_3$-13(-(CH$_2$)$_n$-3,4-epoxide-R')-14-R", where R is a hydrocarbon structure having 3 to 6 carbons, where R' is hydrogen or a methyl group, and R" is a hydrocarbon structure having 1 to 12 carbons, and where n=1 or 2 (carbon numbering on branch assuming n=2);

(ii) an amphoteric surfactant having the chemical formula NH3—R—COOH, where R is a straight, branched, or aromatic hydrocarbon structure having 6 to 24 carbons;

(iii) ethanol solvent for dissolving the amphoteric surfactant;

(iv) water;

(v) nonoxyl-9, which is an aromatic compound with a single phosphate group, and where the phosphate group provides a Lewis acid, and (vi) aluminum sulfate, which in the presence of water provides both the aluminum cation and a small quantity of sulfuric acid, which is a Bronsted-Lowry acid.

The non-ionic surfactant is made from naturally-occurring compositions and is sometimes commercially referred to as a "dodecatriethoxylate" or "EO3" type composition, which is presently commercially available from Hoechst under the trade name "Genapol UDO79."

The attachment process includes various intermediate steps which can lead to one of several resultant chemical structures including a pure crown ether without a transitional metal, a crystahemispherand, a calixarene, a carcerand, a rotoxane, or another form of a host-guest complex. The presence of the chemical unit —C—O—C— can be immediately attached to an aromatic or cyclic compound as long as the end resultant complex completes a cyclic configuration. This reaction stages into repetitive additions of that unit. The larger the $(—C—O—C—)_n$ host molecule, the larger the guest molecule that coordinates with the host.

Non-ionic surfactants with 12 to 16 carbons and three epoxides having a hydro-lipid balance factor of 7–9 will yield an —C—O—C— ether unit. Non-ionic surfactants are formed from alcohols. By treating the alcohol with potassium hydroxide, 96% of the alcohol bonds will form into epoxide groups. By final treatment with aluminum hydroxide, the remaining 4% alcohols will also yield epoxide bonds. Conversely, aluminum sulfate (providing the Bronsted-Lowry acid) will cleave the branched chain, opening the —C—C— bond in the epoxide group that has the oxygen attached. In the presence of zwitterions and at temperatures between 18° C.–46° C. (65° F.–115° F.), the reaction yields relatively large percentages of the ether link.

In this presently most preferred embodiment of the invention, the water is preferably in a stoichiometric proportion of at least 1:1.2 relative to the non-ionic surfactant.

More particularly, it is believed that the basic chemistry is as follows. The host complex is formed by cleaving the branched chain of the non-ionic surfactant. The branched chain contains an epoxide group. According to the presently most preferred embodiment, the key components for cleaving the branched chain and forming the host complex are the presence of an amphoteric surfactant (zwitterion) dissolved in a solvent such as a short chain alcohol, a phosphate group (Lewis acid), an aromatic aryl hydrocarbon. (e.g. attached to phosphate group), aluminum sulfate, and water.

The aluminum sulfate has two roles in this reaction., First, aluminum sulfate in the presence of water and a phosphate group will generate sufficient sulfuric acid to cleave the epoxide branch chain of the non-ionic surfactant. Second, the aluminum sulfate acts as a temporary binding site for the formation of the host complex unit (—C—O—C—)n, where n is at least 3. In the presence of alcohol, the epoxide group breaks between the C—C bond.

In the process, the more polar aromatic group of the phosphated aromatic aryl hydrocarbon replaces the aluminum sulfate creating one of the various host complexes. The alcohol participates in the formation of the host complex unit by sharing electrons while the temperature is ramped up to about 49° C. (120° F). The host complex unit at lower temperatures of 21° C.–32° C. (70° F.–90° F.) can join together by producing an 18-crown-6 ether with a single aromatic ring in the middle to provide rigidity. The internal diameter of 18-crown-6 ether is 7.86A, whereas the external diameter of the benzene ring is 4.56 A.

The less polar end of the aromatic aryl hydrocarbon is at a 75 degree to 90 degree angle from the plane of the host complex. As the temperature increases, the shape of the host complex is that of calixarenes and carcerands without a transition metal in the middle of the structure. Due to the presence of ringed structures in calixarenes and carcerands, several compounds with an aromatic group can provide the rigidity for the host complex.

The zwitterion adds stability to the reaction by partial sharing of electrons during the formation of the host complex. The addition of aromatic compounds with repeating isoprenoid units become the guest in the host complex. The repeating units, whether isoprenoids or polymeric units, provide for subsequent molecular stacking of additional ingredients into the host composition.

At least three molecules of the branched chain non-ionic surfactant is required for the formation of a host complex molecule. Preferably, at least about one weight percent of the host complex in the total composition is formed for the purpose of stabilizing diversely-soluble compounds. Proportionately, one host complex provides inter-molecular attachment sites for three diversely-soluble molecules. This, in turn provides three or more stacking sites for other like molecules. The stacked molecules are then sandwiched between non-ionic surfactant layers.

Without being unnecessarily limited by the theoretical explanation, it is believed that the important factors that drive the host-formation reaction are temperature, solubility, electron transfer, anion balance, and hydro-lipid balance. The anion balance (e.g., phosphate-sulfate balance) is the balance of electrons available from different orbitals due to the molecular configuration of the anions. The crown ethers that are formed are extremely unstable until they become attached within the system based on both nucleophilic and electrophilic reaction. The key to the reaction is the cleavage of the branched chain non-ionic surfactant; i.e., the separation of the $—(CH_2)_n$-3,4-epoxide-R" group. Calixerands, crystahemispherands, calixarenes, carcerands, rotoxanes, or other host molecules can be formed in the process of producing a crown by introducing aromatic compounds prior to full cyclization of the crown ether. Because of greater electron affinity to the paired electrons found in the oxygen molecule and, similarly, in double-bonded shared electrons in cyclic and aromatic compounds, other host complexes can be formed. Refer to FIG. 1.

The subsequent sequence of mixing additional compounds with the host composition allows for stabilization of the one or more host compounds, which then allows for molecular stacking of diversely-soluble compounds. Host compositions begin to stabilize the first addition of the aromatic to the center of the host compound. The host compositions become more stable as more guest compounds are added because the host becomes entrapped rather than entrapping as in the first step of host-guest complex formation.

The remaining system is balanced with assorted surfactants (lamellar layering) allowing for other compounds to be added in a hydro-lipid balanced environment. In the presence of a non-ionic surfactant and an amphoteric surfactant, the apolar ends of the guest molecules will first be directed toward the aqueous phase with the polar ends directed to the crown ether type structure, which also is polar. As the isoprenoid unit extends into the aqueous phase, there will be lamellar layer of similar compounds, especially those that have a ubiqionone structure attached to the hydrocarbon chain. The primary stabilizing component of this compounding method is the introduction of selected compounds during the formation of either the pure 18-crown-6 ether or any resultant compound where the introduced substrate binds to the $(-C-O-C)_n$ complex.

The resultant host-guest complex creates an electronic environment where hydrogen bonding, Van Der Waal forces, and inter-molecular adhesion occurs. And, by partial electron polarity and sharing, the various molecules will align through a process of molecular stacking and layering. It is important to note that this is not the same as forming a 'liposome' system, which requires the presence of what can be various phosphatidyl cholines. Nor is this an emulsion, which is generally created in cold compounding procedures by utilizing high revolutions-per-minute (RPM) mixing, rather than the relatively low RPM mixing preferred according to the inventive formulation processes.

B. Molecular Stacking into Host Composition One or More Bio-active Compounds A process of molecular stacking of one or more bio-active compounds is used in the further formulation of stabilized compositions. The bio-active compounds are selected based on the desired function of the final product and the desired activity level of each of the selected ingredients. The identification and desired bio-active compounds to be stabilized and delivered by the formulation can be determined from the known uses and effectiveness of the bio-effective compound. Numerous classes of compounds are available, including synthetic and natural compounds, as well as natural essential compounds.

Major factors governing the addition of compounds to the host composition environment include:
 (i) the one or more desired bio-affecting compounds desired to be added to create a desired composition for a specific application; and
 (ii) the desired point of attachment to the host complexes.

The systematic addition, i.e., molecular stacking, of the bio-affecting and other desirable ingredients into the host composition is also based on a consideration of the following factors:
 (i) the molecular structure of each ingredient;
 (ii) the solubility of each ingredient compound and the hydro-lipid balance of the composition, and the possibility of changing the solubility characteristics by changing the form of the ingredient, e.g., by using a salt form of the ingredient;
 (iii) in an aqueous composition, the effect of each ingredient on the pH, and the sensitivity of each ingredient to pH; and
 (iv) the temperature required for "setting" or "stacking" the ingredient into the host composition.

1. Molecular Structure

The initial molecular structure required for maintaining stability for diversely-soluble compounds is based on partial polarization of long chain hydrocarbons and the electron protection of aromatic, cyclomatic, and suspected non-metal-containing crown-like ether compounds in the host composition. The initial molecular structure is established through mixing non-ionic surfactants (epoxide groups configured inward protecting the oxygen molecules), establishing divalent charges with the addition of an amphoteric (zwitterion) surfactant, an aromatic group (such as provided by the germicide nonoxyl-9) for initially coordinating with the molecular structure of the host.

Figure 2:
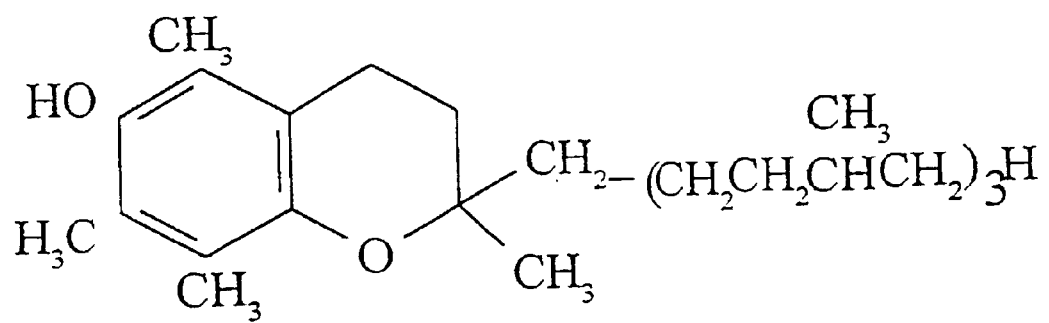
FIG. 2 illustrates an example of a molecular structure for maintaining stability for diversely soluble compounds.
Figure 3:
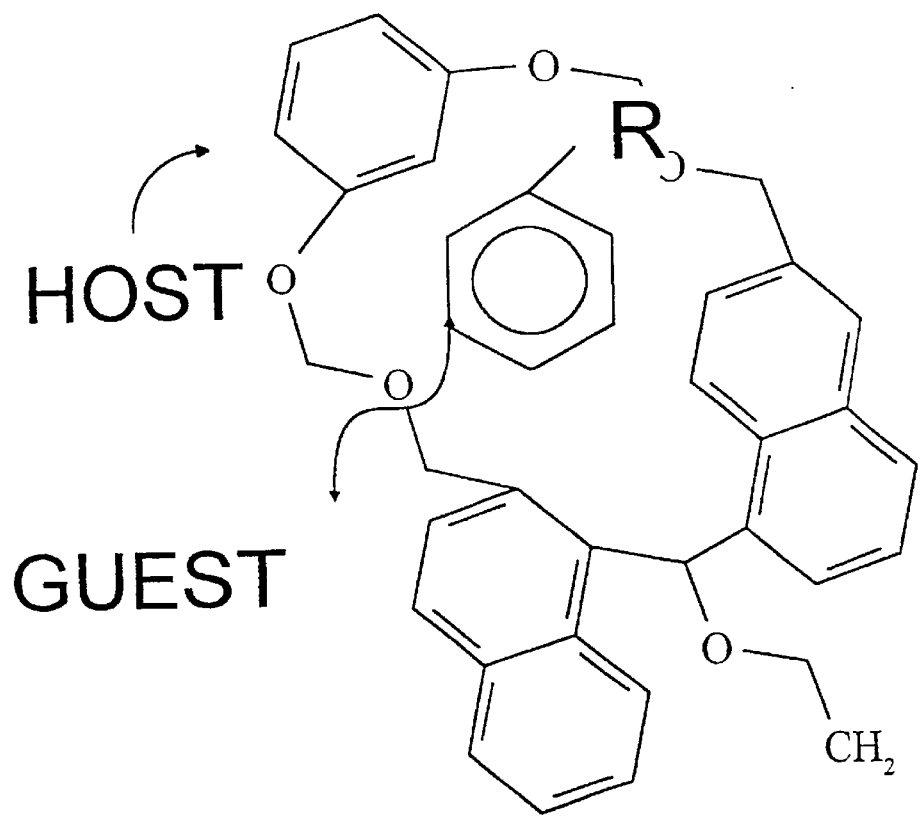
FIG. 3 illustrates a calixerand example of a host-guest relationship.
Figure 4:
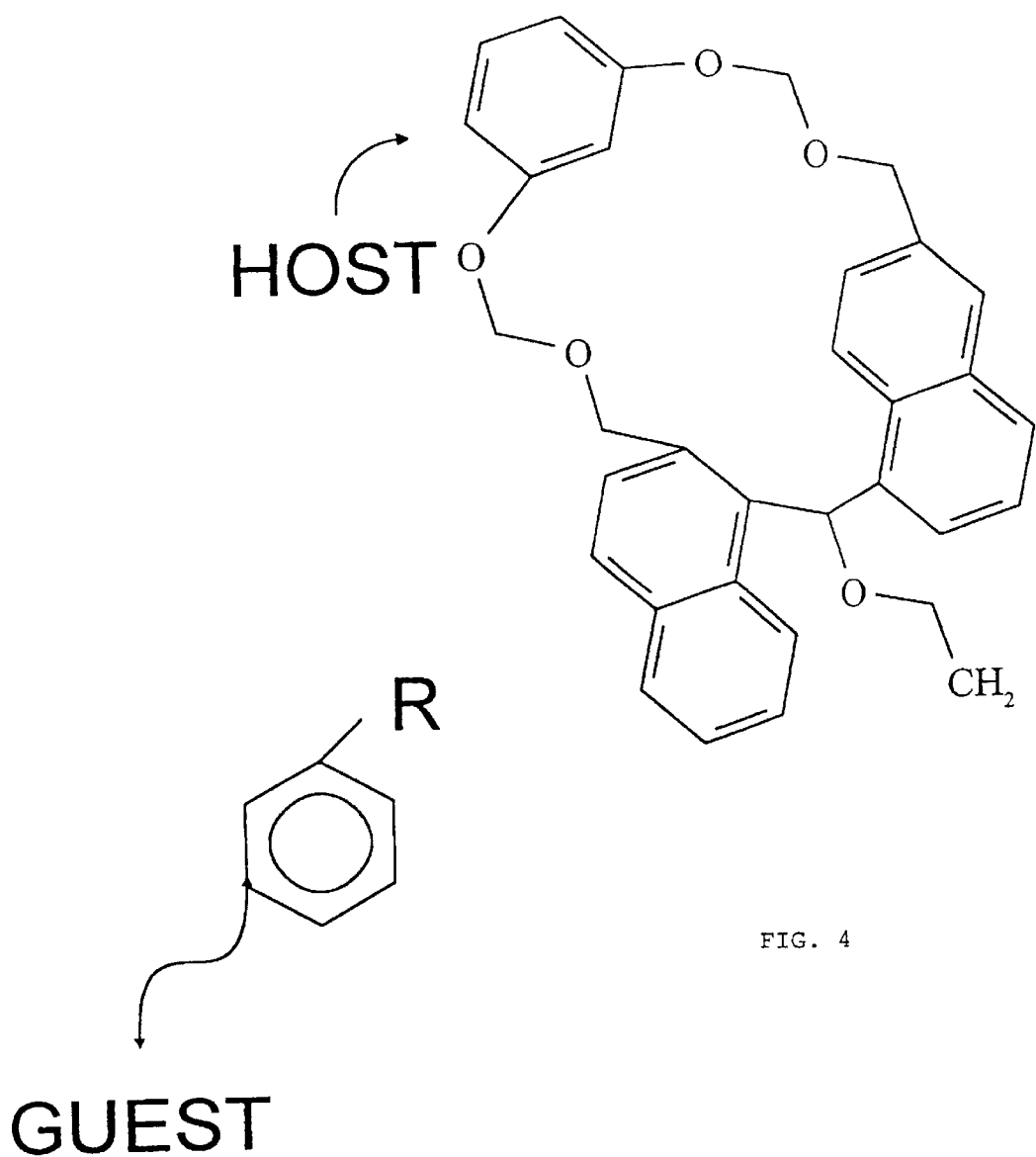
FIG. 4 illustrates a calixerand example of host and an aromatic guest that are not coordinated.

The molecular infrastructure, although similar to a liposome, is not reliant on phosphate compounds such as found in phosphatydal choline. The molecular infrastructure is reliant on the structure of quinones, ubiqinones, menaquinones, and hydroquinones. Although a broad classification of compounds, the molecular structure of quinones and similar structures allow for a molecular stacking in multiple layers due to the diversity of configurations containing cyclics, aromatics, aromatic branched chains, and aromatic cyclic branched chains. Refer to FIGS. 2, 3, and 4.

There are many classes and examples of compounds that can be added to the host-guest composition with the essential factor being the presence of a polar compound having an aromatic ring and a repeating apolar hydrocarbon unit. The variation of the selected compound for stabilization is determined by its stability at a specified temperature and the desired point of attachment in the complex. By selecting a bio-affecting compound that is an active ingredient, the number of compounds that are useful is reduced. The key is the repeating hydrocarbon branch that is found in compounds like alpha-tocopherol, phylioquinones, ubiquinones, menaquinones, and querciquinones. It is also possible to attach polyisoprenoid groups as found in Beta-carotene because the length of the repeating unit between end cyclics.

The selected order is totally dependent on the desired outcome of the bio-affecting product. This is driven by bond angle, electron energy, bond length, and attachment temperature. Once the stabilizing compound, for example, alpha-tocopherol, is selected, the next compound that is desired for the end product is selected. The resulting environment is capable of accepting both water- and lipid-soluble compounds. The key is to select compounds that in later steps are compatible in structure with at least one structural component of the compounds to be later added. This is similar to solubility standards in batch mixing. The difference is that the form of the compound must be able to stack into the host-guest environment of the host composition.

The mix order depends on the molecular stacking concept. The long hydrocarbon chain will easily affiliate or coordinate with the hydrocarbon component (less polar component) of the crown ether host-guest complex or the short branch from the cyclic component of the selected compound will electronically associate with the oxygen component of the crown ether. Further, to stabilize the molecular environment, many natural products can be added prior to a specific compound. For instance, carrot seed oil which is high in Beta-carotene needs to be added prior to highly purified Beta-carotene. The other components of carrot seed oil do not attach to the crown ether environment, but allow for later components (chemicals) to be added. Carrot seed oil, for instance, has flavinoids and fatty acids which allow for later addition through mutual solubility of a wide variety of both natural products like St. John's Wort and other highly-purified chemicals like vitamin B's.

The molecular stacking process is continued on the basis of both attachment to the crown ether and maintaining the hydro-lipid balance as well as future chemicals necessary for an effective bio-affecting compound. This system is based on quinones structures with repeating hydrocarbon units. There is an alternating requirement for the attachment to the crown ether system; if the first compound attached is water soluble, then the next compound must be lipid soluble to maintain the hydro-lipid balance as well as the electrophilic and nucleophilic balance. Nowhere in this process should a compound or series of compounds be added that would substantially diminish that balance. For instance, compounds high in redox potential added in significantly hitch quantity can disrupt that balance. By way of a more particular example, co-enzymes with a quinone structure can be added, but high concentration of flavinoids cannot be added without pre-treatment that would create a reduced compound.

2. Solubility and Hydro-lipid Balance

In setting the order of successive or "stacking" additions, if is essential that the solubility factor and the temperature factor be considered. At the point that a compound like alpha-tocopherol is added, the system has become more hydrophobic. Therefore, it is essential that the next addition be lipid soluble with a water-soluble component to maintain the hydro-lipid balance. It is also essential that this compound be able to electronically associate with the oxygen component of the crown ether.

According to the molecular stacking process, the inter-molecular polarity of the host composition is preferably controlled to be between about 1.8 debye to about 20 debye at 21° C. (70° F.).

According to one approach to controlling the hydro-lipid balance during the molecular stacking, the process includes the steps of:

(a) controlling the inter-molecular polarity of the host composition to be between about 1.8 debye to about 8 debye at 21° C. (70° F.); and (b) mixing at least one lipid-soluble compound with the host composition to obtain a lipi-guest composition.

Subsequently, the process more preferably further includes the steps of:

(a) controlling the inter-molecular polarity of the lipi-guest composition to be between about 8 debye to about 20 debye at 21° C. (70° F.); and (b) mixing at least one water-soluble compound with the second composition to obtain a lipi- and hydro-guest composition.

The inter-molecular polarity of the host composition can be easily controlled by adding water to the composition.

According to another approach to controlling the hydro-lipid balance during the molecular stacking, the process includes the steps of:

(a) controlling the inter-molecular polarity of the host composition to be between about 8 debye to about 20 debye at 21° C. (70° F.): and (b) mixing at least one water-soluble compound with the second composition to obtain a hydro-guest composition.

Subsequently, this process more preferably further includes the steps of:

(a) controlling the inter-molecular polarity of the hydro-guest composition to be between about 1.8 debye to about 8 debye at 21° C. (70° F.); and (b) mixing at least one lipid-soluble compound with the host composition to obtain a lipi- and hydro-guest composition.

3. If in an Aqueous Composition, the Effect on pH

In an aqueous composition, a buffer compound such as betaine is preferably added at some point during the formulation process to help control the pH within a desired range. In the initial formulation of the host composition having the crown ether and a hydro-lipid balanced environment, an amphoteric surfactant $NH_3$—R—COOH is included because of its ability to allow for creation of an electron sharing neutral environment where electrophilic or nucleophilic compounds can be added without substantially altering the established pH. This amphoteric compound, being a zwitterion, al lows for prolonged additions of the above-mentioned types of compounds.

In cases where it is desirable or necessary to control the pH within certain limits, for example, in the case of the need to stabilize a pH-sensitive compound, the pH stabilizing (i.e., buffering) effects of the amphoteric surfactant may need to be overcome. To control the pH, one or more other zwitterions can be added during the formulation process. The choice of the other zwitterions is based on the pH range required to stabilize a pH-sensitive bio-affecting compound.

The desired pH range is preferably maintained by buffering. For example, the pH must be maintained below the pKa of any additional compound or the pKa of any potential bond reaction within the compound to maintain stability within the molecular system. This pKa factor becomes very evident when L-ascorbic acid is one of the compounds to reside in the stable molecular environment. Compounds are added in ratio with their salt form such that the pH is below the pKa.

For example, in the case of a composition for the topical delivery of concentrated Vitamin C, which should be stabilized in a composition having a pH of less than 4.5, a small concentration of a short-length zwitterion, like a betaine, helps adjust and maintain the pH in an acidic range below 4.5. A zwitterion such as allantoin can be preferably added for its additional benefit of having desirable bio-effecting properties, such as softening of the skin. Allantoin has both cyclic and ring structures included, which structures can be taken advantage of for the purposes of selecting the molecular stacking sequence, as well as the zwitterion effect.

Prior to adding the L-ascorbic acid, the pH has to be lowered to below 4. Several choices can be made, all of which are either alpha hydroxy acids or beta-hydroxy acids. Both will work in stabilizing the L-ascorbic acid. The difference is that the selection of a beta-hydroxy acid is more compatible with the bio-affecting application of the product. The amount of the beta-hydroxy acid, in this case salicylic acid, is based on the desired pH. The pH has to be below the C=O bond's pKa of the L-ascorbic acid, 4.5. The salicylic acid, as with most beta-hydroxy acid, is unstable without the combination with its own salt form to allow for there to be pH balance in conjunction with the zwitterion complex previously added. According to a presently most preferred embodiment of the invention for a vitamin C composition, there are several ratios that are preferably followed: Ascorbic acid:ascorbyl palmitate:calcium ascorbate=3:2:1; and Salicylic acid:sodium salicylate=2:1.

To finalize such a Vitamin C product, there are still some chemical lose ends. There is the presence of natural bioflavinoids because of the previous addition of carrot seed oil. To align these compounds into a stable state, another natural product with nearly opposite ratios of compounds needs to be added. It is important to note that, within this process, other compounds can be substituted as long as they meet the crown ether host-guest, hydro-lipid balance in the system, and the molecular stacking requirements. The selection of compounds is entirely based on the bio-affecting system for which it is designed.

4. Temperature Required for Stacking

The temperature must be increased to allow for the complete attachment of the selected first compound. In general, it is preferable to begin stacking the ingredients into the composition in the sequence of highest melting point to lowest. The temperature of the host composition is preferably adjusted (typically heated) to be at least as high as the melting point of the first bio-affecting compound to be added to the mixture to create a molecular environment in which the first bio-affecting compound to be added can be set into the host molecule. By raising the temperature, the resultant reaction allows for the addition of a lipid-soluble compound such as alpha tocopherol or a water-soluble compound such as 7-dehydroxy cholesterol.

For example, in the case of adding alpha tocopherol (Vitamin E), the temperature of the host composition is increased to at least about 49° C. (120° F.). Once the alpha tocopherol has been mixed with the host composition and sets in the lameller layers, the temperature is reduced to below the melting point of the next compound to be added. The speed of mixing and the required amount of time for mixing varies according to volume, but once determined is consistent for that volume.

The resultant mix sets the diverse compounds in a configuration that allows for the first addition of compound containing electrophilic and neuclophilic compound, e g., ascorbyl palmitate. Upon this addition (with temperature control) there exists molecular chains by which either electrophilic or neuclophilic compounds can be added as long as an appropriate pH range is maintained by buffering. The pH must be maintained below the pKa of any additional compound or the pKa of any potential bond reaction within the compound to maintain stability within the molecular system. This pKa factor becomes very evident when L-ascorbic acid is one of the compounds to reside in the stable molecular environment. Compounds are added in ratio with their salt form such that the pH is below the pKa.

Following the completion of the attachment of the alpha tocopheral, other compounds can be added. The next compound to be added is preferably a lipid-soluble derivative of one of the active ingredients in order to begin the basis for molecular stacking of like molecules and reduction of pH, especially in the case of stabilizing the molecular environment for L-ascorbic acid. In this case, because of the future requirement of L-ascorbic acid, ascorbyl palmitate is selected because the palmitate group is lipid soluble and the tail of the ascorbic acid group can electronically attach to the oxygen group of the crown ether system: Note that the system has to be reduced in temperature to accept the ascorbyl palmitate, as it would for other compounds that are bio-affecting, but not necessarily for stabilization of the system.

A pH buffering compound such as betaine should be added soon after the temperature decreases to about 46° C. (115° F.). The temperature is maintained at about 45° C. (112° F.) until all the remaining pH stabilizing ingredients have been mixed together.

C. Resulting Compositions

Following the formulation processes according to the present invention produces a stable product containing one or more bio-affecting compounds. As will be appreciated by those skilled in the art, a wide variety of bio-affecting compositions can be made according to the formulation process. In order to accomplish the additions of these various other compounds, certain process steps have to be completed. The compound has various partially-charged components that can be used to add other essential compounds and maintain stability of the complex. Each addition requires adjustment of temperature of either the added component or the complex itself. For example, in the case of lecithin, a phosphatidyl choline used for oily skin, the addition of the phosphatidyl choline (depending on the precise structure of the phosphatidyl choline) temperature must be adjusted to allow for the compound to intermolecularly bind with the complex. In the case of aloe, used for dry skin, because of its mucopolysaccharide components must be combined with a beta-hydroxy acid to attach with the complex. In the case of Shea Butter, the temperature of the Shea Butter has to be adjusted to become soluble with the complex.

Most additional ingredients are present for effectiveness and bio-affecting applications. Not all ingredients can be added without considering solubility, pH, and temperature.

The resulting composition is highly stable, and certain formulations have been tested to be capable of remaining stable until the air-to-composition ratio in the container is 6:1. At that time there is a 14-day period before one or more of the composition's active ingredients begin to degrade to the point the product composition may become ineffective for one or more of its intended purposes.

D. Process and Formulation Examples

The formulations are based on host-guest formation and chemical structure addition. It is necessary to have similar lipid- or watel-soluble components to the compounds so that the chemicals can either attach to the crown ether type structure or layer by molecular stacking between the compounds. In the case of a pH-sensitive bio-affecting compound such as vitamin C, the pH must below 4.5 before adding the ascorbic acid or, otherwise, the —C=O external to the ring will be subject to oxidation. There are several ratios that are preferably followed: Ascorbic acid:ascorbyl palmitate:calcium ascorbate=3:2:1; and Salicylic acid:sodium salicylate=2:1.

The molecular configuration for quinones requires balancing the attached chain groups to the available electron orbitals from other compounds with similar chain groups. The principle involved is the stacking of compounds with similar aromatic and cyclic structures through the lamellar layer created in the process. The ring structures will tend to stack one upon the other with the apolar ends acting as tails. The isoprenoid units become the apolar end and are aligned in the opposite direction from the polar cyclics. Some cyclics will exhibit a partial polarity based on hydroxylation to the ring.

Each of the following formulations are examples of mixture formulations and steps that can be used to produce a stable composition for the delivery of one or more bio-affecting compounds to a target biological system. The first 10 of the following formulation examples are from actual mixes. The temperatures can vary with reasonable ranges of the precise temperatures used in the examples without departing from the scope and spirit of the examples. The initial phase of the mix preferably includes the step of increasing the temperature to help drive the formation of the host complex. Although the maximum mixing temperature can exceed 49° C. (120° F.), there is a point where the complex will not accept the initial substrate for setting the rigidity of the host-guest complex. This temperature point will vary depending of the guest chemical, but typically is expected to be a maximum of about 540° C. (130° F.).

The RPM of the mix motor can vary depending of the equipment and the type of propeller used in the procedure. However, it is important that the mixing not be unnecessarily fast to minimize the introduction of air (i.e., oxygen) into the composition. Excessive mixing forces may also tend to destabilize the molecular stacking within the mixtures.

Each compound is selected for its bio-affecting capacity within the system and for the stated purposes of the composition. Upon considering the general description of the invention and the following process and formulation examples, those skilled in the art will be able to make numerous modifications and substitutions in the formulations within the scope and spirit of the invention.

Formulation #1—Skin Sloughing/Exfoliation

This formulation is designed to promote skin sloughing. The presence of trans-retinoic acid, a form of retinol (Vitamin A) at the 1.0% or greater level will increase the rate of exfoliation. The first step sets the molecular environment as well as establishes the crown ether host complex. It is important to note that the 6% amino dodecacarboxylic acid is in an ethanol solution. The ethanol provides a solubility factor allowing for the formation of the host complex and the stage for lamellar layering. As the temperature is increased during the mixing steps of the process, the ethanol gradually evaporates.

The addition, in this case the alpha-tocopherol at 41° C. (106° F.), is for the purpose of establishing an attachment to the host-guest complex. The host-guest complex does not go to completion in the procedure until 49° C. (120° F.). For other processes and mixtures, this temperature can vary dependent on the desired guest chemical and the primary decision on which is the first compound to be added to the host composition. As previously mentioned, the first solubility decision drives the mix order and the following decisions as to molecular stacking of additional compounds.

The salicylic acid and sodium salicylate are present to reduce the pH so that ascorbic acid can be added below a pH of 4.5, which is the pKa of the C=O external to the ring structure of the ascorbic acid. It also acts as an exfoliation chemical due to being a beta-hydroxy acid.

The other natural extracts in this formulation example contain natural solublizing compounds allowing for protection from other factors like pH and salt content. These natural products are preferably mixed into the composition before the desired specific compound for biochemical function, in this case, the ascorbic acid.

| Formulation #1 - Skin Sloughing/Exfoliation | | | |
|---|---|---|---|
| Substance | Weight Percent | Temperature ° C. | Mixing RPM |
| Purified water | 9.0 | 16–32 | 15 to 20 |
| 6%, Amino dodeca carboxylic acid | 5.6 | Increase to 41 | |
| Nonoxyl 9 | 3.1 | | |
| Dodecotriethoxylate | 15.0 | | |
| Aluminum Sulfate | 0.003 | | |
| Purified water | 22.0 | | |
| Alpha tocopherol | 5.0 | Increase to 49 Lower to 47 | 20 for 15 minutes |
| Ascorbyl palmitate | 3.4 | | 30–45 for 10 minutes |
| Purified water | 17.0 | Lower to 43 | 30 for 5 minutes |
| Trans-retinoic acid | 1.0 | | 30 for 5 minutes |
| Carrot seed oil | 0.38 | Lower to 42 | 30 for 3 minutes |
| Beta-Carotene | 0.007 | | 30 for 10 minutes |
| Cholecalciferol | 0.007 | | 35 for 10 minutes |
| Calcium ascorbate | 1.2 | Lower to 41 | 45 for 10 minutes |
| Purified water | 9.0 | | 45 for 3 minutes |
| Co-enzyme Q10 | 0.01 | | 45 for 5 minutes |
| Betaine | 0.75 | | 35 for 5 minutes |
| Salicylic acid | 0.41 | | 35 for 10 minutes |
| Sodium salycilate | 0.205 | | 45 for 5 minutes |
| Ascorbic acid | 6.8 | | 45 for 10 minutes |

-continued

| Formulation #1 - Skin Sloughing/Exfoliation | | | |
|---|---|---|---|
| Substance | Weight Percent | Temperature ° C. | Mixing RPM |
| St John's Wort | 0.43 | | 35 for 5 minutes |
| FMN | 0.04 | | 35 for 5 minutes |

Formulation #2-Collagen I Activating Complex

This formulation is designed to maximize the production of collagen I in skin. Therefore, the percentages of ascorbic acid and ascorbic acid derivatives are increased so as to produce a composition having above 8% by weight of water-soluble ascorbic acid. Likewise, the balance needed in the molecular complexing for alpha tocopherol is increased to be above 5% to act in balance to the ascorbic acid and for free radical reduction within the body. With the co-enzyme Q 10 being part of the free radical reduction system, the complex requires a very small, but active, percentage to accelerate the free radical reduction.

The same concept as in Formulation 1 is required for the molecular stacking. In Formulation I only betaine is used for creating a pH buffering balance. Al lantoin, which is a longer chained compound and has better molecular stacking properties, is added due to the increased amounts of active ingredients and additional compounds like orange oil which contains limonene. Allantoin also has properties that increase the integrity of the lipid membrane in the dermal layer. Limonene, found in orange oil is very penetrating in the dermal layer and aids in carrying other compounds across the dermal layer. These additions alone do not count for the complete penetration of the dermal layer and the hyperdermal layer. Lavender is added in the complex because its natural components contain bioflavinoids that are compatible in ring structure and has been reported to promote healing in the skin as does cholecalciferal, a form of Vitamin D. The percent of carrot seed oil is increased relative to the amount in Formulation 1 to increase the concentration of natural beta-carotene and to increase the protection of the beta-carotene by providing a natural screen for 234 nm UV light, which causes beta-carotene to convert to trans-retinol, Vitamin A, which, in turn, would then upset the pH balance of the complex by oxygenating the C=O in the ascorbic acid.

| Formulation #2 - Collagen I Activating Complex | | | |
|---|---|---|---|
| Substance | Weight Percent | Temperature ° C. | Mixing RPM |
| Purified water | 9.0 | 16–32 | 15 to 20 |
| 6% Amino dodeca carboxylic acid | 5.6 | Increase to 41 | |
| Nonoxyl 9 | 3.1 | | |
| Dodecotriethoxylate | 15.0 | | |
| Aluminum Sulfate | 0.003 | | |
| Purified water | 19.0 | | |
| Alpha tocopherol | 5.3 | Increase to 49 Lower to 47 | 20 for 15 minutes |
| Ascorbyl palmitate | 6.0 | | 30–45 for 10 minutes |
| Purified water | 13.0 | Lower to 43 | 31 for 5 minutes |
| Carrot seed oil | 1.0 | Lower to 42 | 30 for 3 minutes |
| Beta-Carotene | 0.025 | | 30 for 10 minutes |
| Cholecalciferol | 0.025 | | 35 for 10 minutes |
| Calcium ascorbate | 3.0 | Lower to 41 | 45 for 10 minutes |
| Purified water | 6.2 | | 45 for 3 minutes |

-continued

Formulation #2 - Collagen I Activating Complex

| Substance | Weight Percent | Temperature ° C. | Mixing RPM |
| --- | --- | --- | --- |
| Co-enzyme Q10 | 0.02 | | 45 for 5 minutes |
| Betaine | 0.25 | | 35 for 5 minutes |
| Allantoin | 0.75 | | 35 for 5 minutes |
| Salicylic acid | 0.8 | | 35 for 10 minutes |
| Sodium salycilate | 0.4 | | 45 for 5 minutes |
| Ascorbic acid | 9.0 | | 45 for 10 minutes |
| St John's Wort | 0.5 | | 35 for 5 minutes |
| Orange oil | 0.5 | | 35 for 5 minutes |
| Lavender | 0.5 | | 35 for 5 minutes |

Formulation #3—Collagen I Activating Formulation for Dry Skin

The primary difference between this formulation and formulation #2, is the presence of Aloe, which contains mucopolysaccharides, amino polylycans, glycolic, and hyaluronic acids. By changing the mix order to eliminate the addition of purified water in step 2, prior to the addition of alpha tocopherol, the molecular stacking results in the reduction of the number the apolar ends creating areas within the complex that will accept the amino and polysaccharide groups without disrupting the solubility balance. Likewise, this formulation can be adjusted for oily skin by changing the aloe to lecithin which is a phosphatidyl choline. The phosphatidyl choline can be added at the end of the order without disrupting the balance within the complex because the phosphate ions will not form liposomes which adsorb oxygen rapidly. The oxygen adsorption will change the pH affecting the C=O of the ascorbic acid, destabilizing the water-soluble ascorbic acid.

Formulation #3 - Collagen I Activating Formulation for Dry Skin

| Substance | Weight Percent | Temperature ° C. | Mixing RPM |
| --- | --- | --- | --- |
| Purified water | 9.0 | 16–32 | 15 to 20 |
| 6% Amino dodeca carboxylic acid | 5.6 | Increase to 41 | |
| Nonoxyl 9 | 3.1 | | |
| Dodecotriethoxylate | 15.0 | | |
| Aluminum Sulfate | 0.003 | | |
| Alpha tocopherol | 5.3 | Increase to 49 Lower to 47 | 20 for 15 minutes |
| Ascorbyl palmitate | 6.0 | | 30–55 for 10 minutes |
| Purified water | 13.0 | Lower to 43 | 32 for 5 minutes |
| Carrot seed oil | 1.0 | Lower to 42 | 30 for 3 minutes |
| Beta-Carotene | 0.025 | | 30 for 10 minutes |
| Cholecalciferol | 0.025 | | 35 for 10 minutes |
| Calcium ascorbate | 3.0 | Lower to 41 | 45 for 10 minutes |
| Purified water | 6.2 | | 45 for 3 minutes |
| Co-enzyme Q10 | 0.02 | | 45 for 5 minutes |
| Betaine | 0.25 | | 35 for 5 minutes |
| Allantoin | 0.75 | | 35 for 5 minutes |
| Salicylic acid | 0.8 | | 35 for 10 minutes |
| Sodium salycilate | 0.4 | | 45 for 5 minutes |
| Ascorbic acid | 9.0 | | 45 for 10 minutes |
| St John's Wort | 0.5 | | 35 for 5 minutes |
| Orange oil | 0.5 | | 35 for 5 minutes |
| Lavender | 0.5 | | 35 for 5 minutes |
| Aloe | 19.0 | | 35 for 5 minutes |

Formulation #4—Relief Crème for Arthritis, Rheumatism, Swelling and Inflammation This formulation is designed to be able to penetrate the dermal and hyperdermal layers to deliver a series of compounds to fibroblast and osteoblast found in joints, tendons, and muscles.

The ascorbic acid activates the production of Collagen I, bringing collagen complex back into balance.

Important to this formulation is Shea Butter which contains a relatively high amount of unsaponifiable fats as compared to other natural oil extracts. The presence of the ratio of unsaponifiable fats to saponifiable fats allows for the stability of the complex without cleaving the Ca bond in the calcium ascorbate due to the reducing capability of unsaponifiable fats. Also, as an active agent, the Shea Butter tends to hold the complex in place on the dermis for a longer period of time allowing for the active components to penetrate the hyperdermal layer and reach the fibroblast, osteoblast, and other tissues. Note that the Shea Butter needs to be heated to be able change from a granular form to a liquid so that the unsaponifiable fats can molecularly stack within the formulation.

Note that the amount of salicylic acid has been increased to 2%. Salicylic acid derivatives, acetyl salicylic acid and methyl salicylate, have been shown to decrease inflammation when taken internally. The delivery system in this complex allows for the salicylic acid and the sodium salicylate to reach the inflamed area, thereby reducing inflammation and swelling.

Formulation #4 - Relief Crème

| Substance | Weight Percent | Temperature ° F. | Mixing RPM |
| --- | --- | --- | --- |
| Purified water | 9.0 | 16–32 | 15 to 20 |
| 6% Amino dodeca carboxylic acid | 5.6 | Increase to 41 | |
| Nonoxyl 9 | 3.1 | | |
| Dodecotriethoxylate | 15.0 | | |
| Aluminum Sulfate | 0.003 | | |
| Purified water | 10.0 | | |
| 7-dehydroxy-cholesterol | 0.5 | Increase to 49 Lower to 47 | 20 for 15 minutes |
| Ascorbyl palmitate | 6.0 | | 30–45 for 10 minutes |
| Purified water | 13.0 | Lower to 43 | 33 for 5 minutes |
| Carrot seed oil | 1.0 | Lower to 42 | 30 for 3 minutes |
| Beta-Carotene | 0.025 | | 30 for 10 minutes |
| Alpha tocopherol | 0.025 | | 35 for 10 minutes |
| Calcium ascorbate | 3.0 | Lower to 41 | 45 for 10 minutes |
| Purified water | 6.2 | | 45 for 3 minutes |
| Co-enzyme Q10 | 0.02 | | 45 for 5 minutes |
| Betaine | 0.25 | | 35 for 5 minutes |
| Allantoin | 0.75 | | 35 for 5 minutes |
| Salicylic acid | 2.0 | | 35 for 10 minutes |
| Sodium salycilate | 1.0 | | 45 for 5 minutes |
| Ascorbic acid | 9.0 | | 45 for 10 minutes |
| St John's Wort | 0.5 | | 35 for 5 minutes |
| Orange oil | 0.5 | | 35 for 5 minutes |
| Lavender | 0.5 | | 35 for 5 minutes |
| Shea Butter | 8.0 | Shea Butter separately heated to 47 before adding | 35 for 5 minutes |

Formulation #5—After Treatment Preparation for Intrusive Skin Care Treatments Like Microdermabrasion and Carbon Dioxide Lasering This formulation is designed to provide relief from procedures that remove layers of skin from the face. The combination of the Shea Butter and the Aloe provide this relief. In order for this formulation to remain stable, the amino polyglycans in the Aloe are added first to provide additional buffering before adding the unsaponifiable fats since the amount of the salicylic acid has been reduced to a level similar to previous formulations. The molecular configuration within the lamellar layering is subject to partial reversal of the micelles that are created if added in a different order.

Formulation #5 - After treatment preparation

| Substance | Weight Percent | Temperature °C. | Mixing RPM |
|---|---|---|---|
| Purified water | 9.0 | 16–32 | 15 to 20 |
| 6% Amino dodeca carboxylic acid | 5.6 | Increase to 41 | |
| Nonoxyl 9 | 3.1 | | |
| Dodecotriethoxylate | 15.0 | | |
| Aluminum Sulfate | 0.003 | | |
| Purified water | 10.0 | | |
| Alpha tocopherol | 5.3 | Increase to 49 Lower to 47 | 20 for 15 minutes |
| Ascorbyl palmitate | 6.0 | | 30–45 for 10 minutes |
| Purified water | 13.0 | Lower to 43 | 34 for 5 minutes |
| Carrot seed oil | 1.0 | Lower to 42 | 30 for 3 minutes |
| Beta-Carotene | 0.025 | | 30 for 10 minutes |
| Cholecalciferol | 0.025 | | |
| Calcium ascorbate | 3.0 | Lower to 41 | 45 for 10 minutes |
| Purified water | 6.2 | | 45 for 3 minutes |
| Co-enzyme Q10 | 0.02 | | 45 for 5 minutes |
| Betaine | 0.25 | | 35 for 5 minutes |
| Allantoin | 0.75 | | 35 for 5 minutes |
| Salicylic acid | 0.8 | | 35 for 10 minutes |
| Sodium salycilate | 0.4 | | 45 for 5 minutes |
| Ascorbic acid | 9.0 | | 45 for 10 minutes |
| St John's Wort | 0.5 | | 35 for 5 minutes |
| Orange oil | 0.5 | | 35 for 5 minutes |
| Lavender | 0.5 | | 35 for 5 minutes |
| Aloe | 9.0 | | 35 for 5 minutes |
| Shea Butter | 9.0 | Shea Butter separately heated to 47 before adding | 45 for 10 minutes |

Formulation #6—Oily Skin Treatment Complex

This formulation is altered from Formulation #5 only by the substitution of lecithin for Aloe and requires a change in percentage due to the properties of phosphatidylcholine.

Formulation #6 - Oily Skin Treatment Complex

| Substance | Weight Percent | Temperature °F. | Mixing RPM |
|---|---|---|---|
| Purified water | 9.0 | 16–32 | 15 to 20 |
| 6% Amino dodeca carboxylic acid | 5.6 | Increase to 41 | |
| Nonoxyl 9 | 3.1 | | |
| Dodecotriethoxylate | 15.0 | | |
| Aluminum Sulfate | 0.003 | | |
| Purified water | 2.0 | | |
| Alpha tocopherol | 5.3 | Increase to 49 Lower to 47 | 20 for 15 minutes |
| Ascorbyl palmitate | 6.0 | | 30–45 for 10 minutes |
| Purified water | 17.0 | Lower to 43 | 36 for 5 minutes |
| Carrot seed oil | 1.0 | Lower to 42 | 30 for 3 minutes |
| Beta-Carotene | .025 | | 30 for 10 minutes |
| Cholecalciferol | .025 | | |
| Calcium ascorbate | 3.0 | Lower to 41 | 45 for 10 minutes |
| Purified water | 6.2 | | 45 for 3 minutes |
| Co-enzyme Q10 | 0.02 | | 45 for 5 minutes |
| Betaine | 0.25 | | 35 for 5 minutes |
| Allantoin | 0.75 | | 35 for 5 minutes |
| Salicylic acid | 0.8 | | 35 for 10 minutes |
| Sodium salycilate | 0.4 | | 45 for 5 minutes |
| Ascorbic acid | 9.0 | | 45 for 10 minutes |
| St John's Wort | 0.5 | | 35 for 5 minutes |
| Orange oil | 0.5 | | 35 for 5 minutes |
| Lavender | 0.5 | | 35 for 5 minutes |
| Lecithin | 6.33 | | 37 for 5 minutes |
| Shea Butter | 7.5 | Shea Butter separately heated to 47 before adding | 45 for 10 minutes |

Formulation #7—Non-greasy Moisturizing Complex

This formulation contains a reducing agent, $FMNH_2$ which, in combination with the bioflavinoids found in St. John's Wort, will attach to the saponifiable fats in Shea Butter. There is an overall decrease in the amount of purified water in the complex. This reduces the chance of destabilizing the ascorbic acid with the reduction in lamellar layering created by having both Aloe and Shea Butter present without the increased amounts of salicylic acid which keeps the pH below 4.0, the C=O pKa of 4.5.

Formulation #7 - Non-greasy Moisturizing Complex

| Substance | Weight Percent | Temperature °C. | Mixing RPM |
|---|---|---|---|
| Purified water | 9.0 | 16–32 | 15 to 20 |
| 6% Amino dodeca carboxylic acid | 5.6 | Increase to 41 | |
| Nonoxyl 9 | 3.1 | | |
| Dodecotriethoxylate | 15.0 | | |
| Aluminum Sulfate | 0.003 | | |
| Purified water | 8.0 | | |
| Alpha tocopherol | 5.3 | Increase to 49 Lower to 47 | 20 for 15 minutes |
| Ascorbyl palmitate | 6.0 | | 30 for 10 minutes |
| Purified water | 17.0 | Lower to 43 | 30 for 5 minutes |
| Carrot seed oil | 1.0 | Lower to 42 | 30 for 3 minutes |
| Beta-Carotene | .025 | | 30 for 10 minutes |
| Cholecalciferol | .025 | | 35 for 10 minutes |
| Phylloquinone | 2.0 | | 35 for 10 minutes |
| Calcium ascorbate | 3.0 | Lower to 41 | 45 for 10 minutes |
| Purified water | 6.2 | | 45 for 3 minutes |
| Co-enzyme Q10 | 0.02 | | 45 for 5 minutes |
| Betaine | 0.25 | | 35 for 5 minutes |
| Allantoin | 0.75 | | 35 for 5 minutes |
| Salicylic acid | 0.8 | | 35 for 10 minutes |
| Sodium salycilate | 0.4 | | 45 for 5 minutes |
| Ascorbic acid | 9.0 | | 45 for 10 minutes |
| St John's Wort | 0.5 | | 35 for 5 minutes |
| $FMNH_2$ | 0.04 | | 35 for 3 minutes |
| Orange oil | 0.5 | | 35 for 5 minutes |
| Lavender | 0.5 | | 35 for 5 minutes |
| Aloe | 6.0 | | 31 for 5 minutes |
| Shea Butter | 3.0 | Shea Butter separately heated to 47 before adding | 45 for 10 minutes |

Formulation #8—Dermal Peeling Complex

This formulation is designed as an acid peel. The pH is lower than the regular pH of 3.5 to 3.0. This formulation illustrates that the use to the host composition for the stabilization and delivery of a single active ingredient, in that this formulation need not contain alpha tocopherol as the host-guest setting compound. Instead, a mucopolysaccharide complex containing amino polyglycans and glycolic acid can be substituted and the mix order changed based on solubility. The different components like glycine are present to stabilize the polar ends of the complex so that the ascorbic acid stability is maintained.

Formulation #8 Dermal Peeling Complex

| Substance | Weight Percent | Temperature °C | Mixing RPM |
|---|---|---|---|
| Purified water | 9.0 | 16–32 | 15 to 20 |
| 6% Amino dodeca carboxylic acid | 5.6 | Increase to 41 | |
| Nonoxyl 9 | 3.1 | | |
| Dodecotriethoxylate | 15.0 | | |
| Aluminum Sulfate | 0.003 | | |
| Purified water | 24.0 | | |
| Mucopolysaccharide | 9.0 | Increase to 49 Lower to 47 | 20 for 15 minutes |
| Ascorbyl palmitate | 3.4 | | 30 to 45 for 10 minutes |
| Purified water | 21.0 | Lower to 43 | 32 for 5 minutes |
| Beta-Carotene | 0.25 | | 30 for 10 minutes |
| Cholecalciferol | 0.25 | Lower to 42 | 35 for 10 minutes |
| Calcium ascorbate | 3.4 | Lower to 41 | 45 for 10 minutes |
| Purified water | 9.1 | | 45 for 3 minutes |
| Glycine | 5.0 | | 45 for 3 minutes |
| Co-enzyme Q10 | 0.01 | | 45 for 5 minutes |
| Betaine | 0.75 | | 35 for 5 minutes |
| Salicylic acid | 2.0 | | 35 for 10 minutes |
| Sodium salycilate | 1.0 | | 45 for 5 minutes |
| Glycolic acid | 3.0 | | 45 for 10 minutes |
| Shea Butter | 10% | Shea Butter separately heated to 47 before adding | 35 for 5 minutes |

Formulation #9—Plant Growth Hormone Delivery System

This formulation is designed as a delivery system for plant growth hormones, diterpenes. This formulation also illustrates that the use to the host composition for the stabilization and delivery of a single active ingredient, in that this formulation need not contain alpha tocopherol as the host-guest setting compound. Instead, a mucopolysaccharide complex containing amino polyglycans and glycolic acid can be substituted and the mix order changed based on solubility. The host complex is first attached to the polar end of the amino polyglycans. The nitrogen complex within the amino group creates a molecular attachment point for the diterpenes. In turn, these isoprenoid units are directed 90 degrees from the crown ether complex providing for lamellar layer of the Co-enzyme Q 10 and the betaine. The chlorophyll, a porphorin compound, attaches parallel to the crown ether complex. Upon penetration of the plant membrane, the diterpene is released into the plant cell.

Formulation #9 - Plant Growth Hormone Delivery System

| Substance | Weight Percent | Temperature °C | Mixing RPM |
|---|---|---|---|
| Purified water | 9.0 | 16–32 | 15 to 20 |
| 6% Amino dodeca carboxylic acid | 5.6 | Increase to 41 | |
| Nonoxyl 9 | 3.1 | | |
| Dodecotriethoxylate | 15.0 | | |
| Aluminum Sulfate | 0.003 | | |
| Purified water | 24.0 | | |
| Mucopolysaccharide | 15.0 | Increase to 49 Lower to 47 | 20 for 15 minutes |
| Diterpene | 25.0 | Lower to 42 | |
| Co-enzyme Q10 | 0.5 | | |
| Purified water | 11.0 | Lower to 41 | 35 for 5 minutes |
| Betaine | 1.0 | | 45 for 5 minutes |
| Chlorophyll | 10.0 | | 35 for 5 minutes |

Formulation #10—Antioxidant Treatment for Rough Dry Skin

This formulation is designed to penetrate the dermal layer when it has become 'sequacious', which is an overlayering condition of the skin. This formulation illustrates the ability of the formulation process to provide a stable complex with primarily lipid-soluble components.

Formulation #10 Antioxidant Treatment for Rough Dry Skin

| Substance | Weight Percent | Temperature °F | Mixing RPM |
|---|---|---|---|
| Purified water | 9.0 | 16–32 | 15 to 20 |
| 6% Amino dodeca carboxylic acid | 5.6 | Increase to 41 | |
| Nonoxyl 9 | 3.1 | | |
| Dodecotriethoxylate | 15.0 | | |
| Aluminum Sulfate | 0.003 | | |
| Purified water | 24.0 | | |
| Mucopolysaccharide | 15.0 | Increase to 49 Lower to 43 | 20 for 15 minutes |
| Alpha tocopherol | 10.0 | | |
| Co-enzyme Q10 | 0.25 | Lower to 42 | |
| Purified water | 15.0 | Lower to 41 | 35 for 5 minutes |
| Betaine | 0.5 | | 45 for 5 minutes |
| Ascorbyl palmitate | 1.0 | | |
| St John's Wort | 1.0 | | 35 for 5 minutes |

Formulation #11—Partial Antioxidant and Chemical Peel Treatment for Dry Skin

This formulation is designed to penetrate the dermal layer acting as a chemical peel. This formulation illustrates the ability of the formulation process to provide a stable composition by first mixing a water-soluble bio-affecting compound with the host composition.

Formulation #11 - Partial Antioxidant and Chemical Peel Treatment for Dry Skin

| Substance | Weight Percent | Temperature °C | Mixing RPM |
|---|---|---|---|
| Purified water | 9.0 | 16–32 | 15 to 20 |
| 6% Amino dodeca carboxylic acid | 5.6 | Increase to 41 | |
| Nonoxyl 9 | 3.1 | | |
| Dodecotriethoxylate | 15.0 | | |
| Aluminum Sulfate | 0.003 | | |
| Salicylic acid | 1.0 | Increase to 49 | 20 for 40 minutes |
| Ascorbic acid | 11.0 | Lower to 44 | 20 for 15 minutes |
| Alpha tocopherol | 6.0 | Lower to 41 | 35 for 20 minutes |
| Purified water | 47.3 | Lower to 41 | 35 for 5 minutes |
| Sodium salicylate | 0.5 | | 45 for 5 minutes |
| Betaine | 0.5 | | 45 for 5 minutes |
| St John's Wort | 1.0 | | 35 for 5 minutes |

Formulation #12—Metallo Complexes for Anti-oxidant, Moisturizing Sun Protectors

This formulation is designed to provide sun protection from UV-A/UV-B wave lenghts by including metallo complexes known to provide in vivo and in vitro coverage, i.e., zinc oxide and titanium dioxide. Additional ingredients are preferably added for anti-oxidant benefits, occlusion, and moisturizing capabilities.

Formulation #12 - Metallo Complexes for Sun Protectors

| Substance | Weight Percent | Temperature ° C. | Mixing RPM |
|---|---|---|---|
| Purified water | 9.0 | 16–32 | 15 to 20 |
| 6% Amino dodeca carboxylic acid | 5.6 | Increase to 49 | |
| Nonoxyl 9 | 3.1 | | |
| Dodecotriethoxylate | 15.0 | | |
| Aluminum Sulfate | 0.003 | | |
| Titanium Dioxide | 2.0 | Lower to 46 | 30 to 45 minutes |
| Carrot Seed Oil | 0.1 | | |
| Melatonin | 0.1 | | |
| Zinc Oxide | 12.5 | | |
| Purified water | 12.0 | | |
| Pentasilicone | 1.0 | Maintain at 46 | 45 to 60 minutes |
| Vegetable Glycerine | 8.05 | | |
| Shea Butter | 5.4 | | |
| Alpha tocopherol | 2.1 | | |
| Ascorbyl Palmitate | 8.5 | | |
| Aloe | 4.3 | | |
| Grapeseed Oil | 1.3 | Maintain at 46 | 60 to 90 minutes |
| Purified water | 19.3 | | |
| Gamma Oryzanol | 1.0 | | |
| Cyclomethisilicone | 5.0 | | |

Conclusion

These and other aspects of the invention will be apparent to those skilled in the art. The illustrative examples discussed herein are not for the purpose of pointing out what an infringement would be, but are only for the purpose of illustrating various aspects of the invention. Those skilled in the art will recognize that numerous variations in the examples according to the formulation processes and compositions are possible, and that numerous substitutions of compounds can be made without departing from the scope and spirit of the invention.

What is claimed is:

1. A process of making a host composition having a host capable of accepting a guest, the process comprising mixing, in any order:

(i) a non-ionic surfactant selected from the group consisting of compounds having a chemical structure:

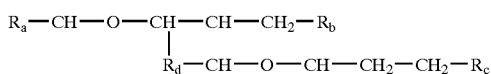

where "—CH—O—CH—" represents an epoxide-group, where $R_a$ and $R_b$ are hydrocarbons that can be the same or different, where at least one of the $R_a$ and $R_b$ hydrocarbons includes an epoxide group within 3 carbons of the hydrocarbon attachment to contribute to the desired hydro-lypid balance of 7–9, where $R_c$ is hydrogen or a methyl group, and where $R_d$ is a methylene group (—$CH_2$—), an ethyl group(—$CH_2$—$CH_2$—), or a structurally-equivalent link with a bond length range about the same as or shorter than that provided by an ethyl group, and having a hydro-lipid balance in the range of 7–9, or any combination of two or more thereof;

(ii) in a stoichiometric proportion of at least 1:6 relative to the non-ionic surfactant, an amphoteric surfactant selected from the group consisting of organic compounds-having the chemical formula NH3—R—COOH, where R is a straight, branched, or aromatic hydrocarbon structure having 6–24 carbons, or any combination of two or more thereof;

(iii) at least a sufficient amount of a solvent to dissolve the amphoteric surfactant, the sol vent comprising one or more compounds selected from the group consisting of water, alcohols having straight or branched hydrocarbon structure having up to 6 carbons, glycosamionoglucans, or any combination of two or more of the foregoing;

(iv) in a stoichiometric proportion of at least 1:240 relative to the non-ionic surfactant, an aromatic selected from the group consisting of compounds having at least one aromatic five- or six-member ring, or any combination of two or more thereof;

(v) in a stoichiometric proportion of at least 1:240 relative to the non-ionic surfactant, of an aluminum cation;

(vi) in a stoichiometric proportion of at least 1:1200 relative to the non-ionic surfactant of at least one Lewis acid that is not a Bronsted-Lowry acid;

(vii) at least 0.003 molar concentration of at least one Bronsted-Lowry acid.

2. A process according to claim 1, further comprising the step of: controlling the inter-molecular polarity of the host composition to be between about 1.8 debye to about 20 debye at 21° C. (70° F.).

3. The process according to claim 2, further comprising the steps of:

(a) controlling the inter-molecular polarity of the host composition to be between about 1.8 debye to about 8 debye at 21° C. (70° F.); and (b) mixing at least one lipid-soluble compound with the host composition to obtain a lipi-guest composition.

4. The process according to claim 3, further comprising the steps of:

(a) controlling the inter-molecular polarity of the lipi-guest composition to be between about 8 debye to about 20 debye at 21° C. (70° F.); and (b) mixing at least one water-soluble compound with the second composition to obtain a lipi- and hydro-guest composition.

5. The process according to claim 3, wherein the inter-molecular polarity of the host composition is controlled by adding water.

6. The process according to claim 2, further comprising the steps of:

(a) controlling the inter-molecular polarity of the host composition to be between about 8 debye to about 20 debye at 21° C. (70° F.); and (b) mixing at least one water-soluble compound with the second composition to obtain a hydro-guest composition.

7. The process according to claim 6, further comprising the steps of:

(a) controlling the inter-molecular polarity of the hydro-guest composition to be between about 1.8 debye to about 8 debye at 21° C. (70° F.); and (b) mixing at least one lipid-soluble compound with the host composition to obtain a lipi- and hydro-guest composition.

8. The process according to claim 1, wherein the non-ionic surfactant is dodecatriethoxylate.

9. The process according to claim 1, wherein the amphoteric surfactant is amino dodecacarboxylic acid.

10. The process according to claim 1, wherein the polarity of the solvent is sufficiently high whereby the solvent has an electrical conductance of at least 1 micro mho measured at a temperature of 21° C. (70° F.).

11. The process according to claim 10, wherein the polarity of the solvent is sufficiently high such that the solvent has an electrical conductance in the range of about 1–10 micro mho measured at a temperature of 21° C. (70° F.).

12. The process according to claim 1, wherein the solvent comprises ethanol.

13. The process according to claim 1, wherein the solvent comprises water.

14. The process according to claim 13, wherein the aromatic and the Lewis acid are both provided by the single compound nonoxyl-9.

15. The process according to claim 13, wherein the aluminum cation and the Bronsted-Lowry acid are both provided by aluminum sulfate, which at least partially reacts with water in the solvent to produce sulfuric acid as the Bronsted-Lowry acid.

16. The process according to claim 13, wherein the pH of the solution is maintained between 4.5 and 5.5.

17. The process according to claim 1, wherein the temperature of the mixture is controlled to be within the range of about 21° C. (70° F.) to about 54° C. (130° F.) until the reaction is substantially complete.

18. The process according to claim 1, wherein the temperature of the mixture is controlled to be within the range of about 38° C. (100° F.) to about 54° C. (130° F.) for at least 15 minutes.

19. The process according to claim 3, wherein the lipid-soluble compound is selected from the group consisting of: alpha tocopherol, alpha tocopherol ester, co-enzymes, ubiquinones, menaquinones, phylloquinones, 7-dehydroxy cholesterol, steroids, bioflavinoids, terpenes, saponified fatty acids, unsaponified fats, glycerophospholipids, and any combination of two or more of the foregoing.

20. The process according to claim 19, wherein, at the time of mixing the lipid-soluble compound, the temperature of the host composition is controlled to be at least as high as the melting point of the lipid-soluble compound.

21. The process according to claim 7, wherein the lipid-soluble compound is selected from the group consisting of: alpha tocopherol, alpha tocopherol ester, co-enzymes, ubiquinones, menaquinones, phylloquinones, 7-dehydroxy cholesterol, steroids, bioflavinoids, terpenes, saponified fatty acids, unsaponified fats, glycerophospholipids, and any combination of two or more of the foregoing.

22. The process according to claim 21, wherein, at the time of mixing the lipid-soluble compound, the temperature of the host composition is controlled to be at least as high as the melting point of the lipid-soluble compound.

23. The process according to claim 4, wherein the water-soluble compound is selected from the group consisting of: ascorbic acid, ascorbyl salts, 7-dehydroxy cholesterol, alpha-hydroxy acids, beta-hydroxy acids, glycolic acids, isoprenoids, bioflavinoids, fatty acids, glycosaminoglucans, flavin mono nucleotides, flavin mono nucleotide derivatives, diterpenes, glycerophospholipids, beta-carotene, trans retinol, trans retinoic acid, allontoin, nonoxyl-9, betaine, and any combination of two or more of the foregoing.

24. The process according to claim 23, wherein, at the time of mixing the water-soluble compound with the second composition, the temperature of the host composition is controlled to be lower than the melting point of the, lipid-soluble compound.

25. The process according to claim 6, wherein the water-soluble compound is selected from the group consisting of: ascorbic acid, ascorbyl salts, 7-dehydroxy cholesterol, alpha-hydroxy acids, beta-hydroxy acids, glycolic acids, isoprenoids, bioflavinoids, fatty acids, glycosaminoglucans, flavin mono nucleotides, flavin mono nucleotide derivatives, diterpenes, glycerophospholipids, beta-carotene, trans retinol, trans retinoic acid, allontoin, nonoxyl-9, betaine, and any combination of two or more of the foregoing.

26. The process according to claim 25, wherein, at the time of mixing the water-soluble compound with the second composition, the temperature of the host composition is controlled to be lower than the melting point of the lipid-soluble compound.

27. The process according to claim 1, further comprising the step of: mixing at least one transition metal compound with the host composition to obtain a metallo-guest composition.

28. The process according to claim 27, wherein the transition metal compound is selected from the group consisting of zinc oxide and titanium dioxide and any combination thereof.

29. A process of making a host composition having a host capable of accepting a guest, the process comprising mixing, in any order:

(i) a non-ionic surfactant comprising dodecatriethoxylate;

(ii) in a stoichiometric proportion of at least 1:6 relative to the non-ionic surfactant, an amphoteric surfactant comprising amino dodecacarboxylic acid;

(iii) at least a sufficient amount of a solvent to dissolve the amphoteric surfactant, the solvent comprising one or more compounds selected from the group consisting of alcohols having straight or branched hydrocarbon structure having up to 6 carbons, or any combination of two or more of the foregoing;

(iv) in a stoichiometric proportion of at least 1:1.2 relative to the non-ionic surfactant, water;

(v) in a stoichiometric proportion of at least 1:240 relative to the non-ionic surfactant, nonoxyl-9;

(vi) in a stoichiometric proportion of at least 1:240 relative to the non-ionic surfactant, aluminum sulfate.

30. The product produced by a process according to any one of claims 1–29.

* * * * *

UNITED STATES PATENT AND TRADEMARK OFFICE
CERTIFICATE OF CORRECTION

PATENT NO. : 6,676,951 B1
DATED : January 13, 2004
INVENTOR(S) : Charles Walton Champ and Karen June Kinzer It is certified that error appears in the above-identified patent and that said Letters Patent is hereby corrected as shown below:

<u>Title page,</u>
Item [57], ABSTRACT,
Line 22, delete "(I)";

<u>Column 8,</u>
Line 7, delete "lo" and insert -- to --;
Line 8, delete "in" first occurrence;
Line 10, delete "tdiversely-solublensitional" and insert -- transitional --;
Line 32, delete "structudiversely-solublelly" and insert -- structurally --;
Lines 33 and 36, delete "diversely-solublenge" and insert -- range --;
Line 38, after "thereof" insert -- . --;
Lines 41-42, delete "prefediversely-solublebly" and insert -- preferably --;

<u>Column 9,</u>
Line 58, delete "," after -- . --;

<u>Column 13,</u>
Line 14, delete "if" and insert -- it --;

<u>Column 14,</u>
Line 6, delete "al lows" and insert -- allows --;

<u>Column 15,</u>
Line 44, delete ":" and insert -- . --;

<u>Column 16,</u>
Line 61, delete "540" and insert -- 54 --;
Line 62, delete "of" second occurrence and insert -- on --;

<u>Column 18,</u>
Line 20, delete "Q 10" and insert -- Q10 --;
Line 25, delete "Al lantoin" and insert -- Allantoin --;

<u>Column 19,</u>
Line 20, delete "polylycans," and insert -- polyglycans, --;

UNITED STATES PATENT AND TRADEMARK OFFICE
CERTIFICATE OF CORRECTION

PATENT NO.   : 6,676,951 B1
DATED        : January 13, 2004
INVENTOR(S)  : Charles Walton Champ and Karen June Kinzer It is certified that error appears in the above-identified patent and that said Letters Patent is hereby corrected as shown below:

Column 20,
Line 14, after "able" insert -- to --;

Column 23,
Line 47, delete "Q 10" and insert -- Q10 --;

Column 26,
Line 8, delete "compounds-having" and insert -- compounds having --;
Line 13, delete "sol vent" and insert -- solvent --;

Column 28,
Line 14, delete the "," after "the" second occurrence.

Signed and Sealed this

Seventh Day of September, 2004

JON W. DUDAS
*Director of the United States Patent and Trademark Office*